United States Patent [19]

Hadas

[11] Patent Number: 5,609,875
[45] Date of Patent: Mar. 11, 1997

[54] SKIN WHITENING COMPOSITION

[75] Inventor: Nira Hadas, Ramat-Gan, Israel

[73] Assignee: Fischer Pharmaceuticals Ltd., Ramat Gan, Israel

[21] Appl. No.: 402,445

[22] Filed: Mar. 13, 1995

[30]     Foreign Application Priority Data

Mar. 17, 1994  [IL]  Israel ......................................... 109012

[51] Int. Cl.$^6$ ........................... A61K 35/78; A61K 7/135; A61K 6/00
[52] U.S. Cl. ........................ 424/195.1; 424/62; 424/401; 514/557; 514/844
[58] Field of Search ................................ 424/195.1, 401, 424/62; 514/557, 844

[56]               References Cited

U.S. PATENT DOCUMENTS 5,164,185  11/1992  Charpin et al. ......................... 424/401
5,420,106  6/1995  Parab ............................................ 514/2

OTHER PUBLICATIONS

Chem Absts. 90(1):6570r, 1979.

*Primary Examiner*—John W. Rollins
*Attorney, Agent, or Firm*—Keck, Mahin & Cate

[57]              ABSTRACT

Cosmetic skin whitening compositions based on the combination of plant extracts and alpha-, beta-hydroxy or keto acids, amides, ammonium salts, other inorganic salts and esters of these. The compositions may also contain one or more of UVA filters, UVB filters, derivatives of vitamin E, Vitamin C or its derivatives. The compositions may contain conventional additives. A preferred plant extract is that of licorice (Glycyrrhiza Glabra) and of related plant species. Such compositions also prevent to a large extent formation of skin spots.

10 Claims, No Drawings

SKIN WHITENING COMPOSITION

FIELD OF THE INVENTION

The invention relates to skin whitening compositions. These are cosmetic compositions based on the extracts of certain plants in combination with certain alpha or beta hydroxy or keto acids and their amides, ammonium or inorganic salts and their esters. The compositions inhibit melanin formation, amongst others by the inhibition of tyrosinase activity.

BACKGROUND OF THE INVENTION

Various cosmetic preparations are on the market which are intended for the whitening of skin and which are also intended to prevent the formation of skin spots. These comprise a variety of components, part of which are synthetic products and which may have deleterious side effects. The activity of such preparations varies and in some cases a very slight effect is obtained, if at all. The present invention provides an improved cosmetic skin whitening composition with enhanced efficacy.

The present invention relates to novel cosmetic composition for topical application which result in whitening of the skin and which prevent to a large extent further formation of skin spots.

The composition of the invention comprise in combination extracts of the root of Glycyrrhiza glabra or associated species in a powder form which contain approx. 10% of glabridine which are effective in reducing melanin synthesis by inhibiting tyrosinase activity, together with alpha or beta hydroxy or keto acids.

Each component mentioned in this invention demonstrates effectiveness in fade-out of human skin spots. When the components are blended they produce a significant increase (p-value 0.01) in tyrosinase inhibitory activity. This activity was greater than the sum of the inhibitory activity of each of the components alone.

It seems, based on tests we have performed, that the synergistic effects are also due to the fact that alpha or beta hydroxy acids or a keto acid, their esters as well as inorganic or organic salts, such as glycolic acid, Citric acid, Lactic acid, Malic acid, Tartronic acid, Tartaric acid, Glucoronic acid, Pyruvic acid, 2-hydroxy isobutyric acid, Ethyl or Methyl pyruvate when applied topically in a concentration between 0.5% and 30% decrease corneocytes cohesion which results in reducing thickness of the stratum corneum and therefore increasing penetration of the active ingredients.

Plant extracts which can be used are for example, from six varieties of glycyrrhiza glabra Linne, Glycyrrhiza uralensis Fisher, Glycyrrhiza inflator Batalin or associated species from the Leguminosae family of plants.

The product is extracted from the root of the plant. 1 kg of the root from Licorice is mixed with 10 liters of anhydrous ethanol and heated under reflux for 5 hours. The decoction is collected and concentrated under reduced pressure. To this extract 1 liter of ethyl acetate is added and heated under reflux for 5 hours. The filtrate is concentrated under reduced pressure and dried. Yellow to red powder is obtained.

Generally the compositions will contain from about 0.005% wt to about 5% wt of the dried plant extract, the preferred range being between 0.05%–0.2%.

Amongst the a-hydroxy, β-hydroxy, or keto acids, their organic or inorganic salts or esters are: glycolic acid, lactic acid, malic acid, citric acid, Pyruvic acid, Tartaric acid, Salicylic acid, etc., The quantity of alpha or beta hydroxy or keto acid used in the compositions will vary between about 0.1% to about 30% the preferred range being from about 1% to about 8%.

Amongst optional ingredients of such skin whitening compositions there may be mentioned sun filter in the UVA & UVB range, vitamins or their derivatives, such as Vitamin C or E.

Extensive experiments have demonstrated that the cosmetic compositions of the invention result in an effective skin whitening, and it is believed that this is due to the synergistic activity of the mixed ingredients on the inhibition of tyrosinase, which normally converts tyrosine to melanin.

Furthermore, by reducing stratum corneum thickness, this synergistic effect is enhanced.

Test in vitro on the effect of glycolic acid and glycyrrhiza dry extract on tyrosinase inhibitory activity has been carried out based on the Methodology of Maruzene Pharmaceuticals. The anti-tyrosinase activity was investigated by colorimeter comparison at 475 nm and calculated as percentage of the inhibitory activities. (Attached are the results).

TABLE 1

In vitro tyrosinase inhibitory activity of Glycolic acid

| Glycolic acid concentration mg/5 ml. | % Tyrosinase Inhibition Test 1. | % Tyrosinase Inhibition Test 2. |
|---|---|---|
| 7.21 | 10.74 | 27.81 |
| 1.61 | 7.60 | 21.32 |
| 0.805 | 5.64 | 16.11 |
| 0.42 | 4.86 | 9.12 |

TABLE 3

In vitro tyrosinase inhibitory activity of Leguminosae species extract with Glycolic acid

| Glycolic acid conc. mg/5 ml. | Leguminosae species ext. conc. mg/5 ml. | Test 1 a | Test 1 b | Test 2 a | Test 2 b |
|---|---|---|---|---|---|
| 7.21 | 0.04 | 39.23 | 63.28 | 60.45 | 70.02 |
| 1.61 | 0.04 | 36.09 | 60.03 | 53.96 | 66.85 |
| 0.805 | 0.04 | 34.13 | 55.44 | 48.75 | 60.41 |
| 0.42 | 0.04 | 33.35 | 53.73 | 41.76 | 48.94 | a Theoretical inhibitory activity - Sum of % inhibition of Leguminosae species extract and different concentrations of Glycolic acid.
b In vitro % inhibitory activity of the combination of Leguminosae species extract and Glycolic acid.

TABLE 2

In vitro tyrosinase inhibitory activity of Leguminosae species extract

| Leguminosae species extract mg/5 ml. | % Tyrosinase Inhibition Test 1. | % Tyrosinase Inhibition Test 2. |
|---|---|---|
| 0.04 | 28.49 | 32.64 |
| 0.02 | 11.74 | 19.94 |
| 0.01 | 8.67 | 16.48 |

TABLE 2-continued

In vitro tyrosinase inhibitory activity of Leguminosae species extract

| Leguminosae species extract mg/5 ml. | % Tyrosinase Inhibition Test 1. | % Tyrosinase Inhibition Test 2. |
|---|---|---|
| 0.005 | 5.18 | 12.70 |

The following results of experiments carried out with human volunteers are representative of a series of experiments. These are by way of illustration only and are not to be construed in a limitative manner.

Test on human volunteers was conducted according to HRL protocol.

In the following examples the quantities are in weight-%. All designations are according to CTFA names.

Example 1: Cream

| Licorice extract | 0.15 |
|---|---|
| Cream base, up to | 100.00 |

The effect is one of inhibition of tyrosinase activity, which converts tyrosin to melanin.

Example 2: Cream

| Licorice extract | 0.15 |
|---|---|
| Glycolic acid | 8.00 |
| Cream base, up to | 100.00 |

TEST RESULTS

Example 1

Cream Licorice ext.—0.15 Cream Base ad 100
Number of Spots:
  Nine of the sixteen subjects showed at least 1 level of diminution of the number of spots.
  Six of the subjects remained at baseline (56.2%).
Color of Spots:
  Ten of the sixteen subjects improved at least one grade in the color of the spots on the treated hand.
  Five of the subject remained at base line (62.5%).
Level of contrast:
  Twelve of the sixteen subjects had at least 1 level of reduced contrast on treated hands (75%).
Example 2
Number of spots:
  Thirteen of the sixteen subjects showed at least 1 level of diminution to the number of spots.
  Three of the subjects remained at base line (81.25%).
Color of spots:
  Fourteen subjects of the sixteen subjects improved at least one grade in the color of the spots on the treated hand (87.5%).
Level of contrast:
  All the subjects had at least 1 level of reduced contract on treated hands 100%.

Experiments were carried out with extracts of other plants, mentioned above, under similar conditions, and similar results were obtained.

In the following examples the quantities are in weight %

| 3) Magnesium aluminium silicate | 0.5 |
|---|---|
| Xanthan gum | 0.5 |
| Cetearyl alcohol (and) Ceteareth 20 | 1 |
| Glyceryl stearate (and) PEG 100 stearate | 4 |
| Preservatives | 9.5 |
| Licorice ext. | 0.1 |
| Glycolic acid | 5 |
| Ammonium hydroxide q.s. to pH | 4 |
| Hydrogenated polyisobutene | 4 |
| Purified water add | 100 |
| 4) Magnesium aluminium silicate | 0.5 |
| Xanthan gum | 0.5 |
| Cetearyl alcohol (and) Ceteareth 20 | 1 |
| Glycyeryl stearate (and) PEG 100 stearate | 4 |
| Preservatives | 9.5 |
| Licorice ext. | 0.1 |
| Lactic acid | 5 |
| Ammonium hydroxide q.s. to pH | 4 |
| Hydrogenated polyisobutene | 4 |
| Purified water add to | 100 |
| 5) Magnesium aluminium silicate | 0.5 |
| Xanthan gum | 0.5 |
| Cetearyl alcohol (and) Ceteareth 20 | 1 |
| Glyceryl stearate (and) PEG 100 stearate | 4 |
| Preservatives | 9.5 |
| Licorice ext. | 0.1 |
| Pyruvic acid | 8 |
| Sodium hydroxide | 4 |
| Hydrogenated polyisobutene | 4 |
| Purified water add to | 100 |
| 6) Licorice ext | 0.05 |
| Salicylic acid | 0.5 |
| Polysorbate | 5 |
| Ethanol add to | 100 |
| 7) Magnesium aluminium silicate | 0.5 |
| Xanthan gum | 0.5 |
| Cetearyl alcohol (and) Ceteareth 20 | 1 |
| Glyceryl stearate (and) PEG 100 stearate | 4 |
| Preservatives | 9.5 |
| Magnesium ascorbyl phosphate | 1 |
| Licorice ext. | 0.1 |
| Glycolic acid | 5 |
| Kojic acid | 0.5 |
| Ammonium hydroxide q.s. to pH | 4 |
| Hydrogenated polyisobutene | 4 |
| Octyl methoxycinnamate | 7.5 |
| Tiol | 2 |
| Purified water add | 100 |
| 8) Magnesium aluminium silicate | 0.5 |
| Xanthan gum | 0.5 |
| Cetearyl alcohol (and) Ceteareth 20 | 1 |
| Glyceryl stearate (and) PEG 100 stearate | 4 |
| Preservatives | 9.5 |
| Licorice ext. | 0.1 |
| Lactic acid | 5 |
| Ammonium hydroxide q.s. to pH | 4 |
| Hydrogenated polyisobutene | 4 |
| Octyl methoxycinnamate | 0.5 |
| Benzophenone | 3 |
| Butyl methoxydibenzoylmethane | 0.5 |
| Purified water add to | 100 |
| 9) Magnesium aluminium silicate | 0.5 |
| Xanthan gum | 0.5 |
| Cetearyl alcohol (and) Ceteareth 20 | 1 |
| Glyceryl stearate (and) PEG 100 stearate | 4 |

|  |  |
| --- | --- |
| Preservatives | 0.5 |
| Licorice ext. | 3.0 |
| Pyruvic acid | 8 |
| Sodium hydroxide | 4 |
| Hydrogenated polyisobutene | 4 |
| Octyl salicylate | 4 |
| Octocrylene | 3 |
| Zno | 1 |
| Purified water add to | 100 |
| 10) Magnesium aluminium silicate | 0.5 |
| Xanthan gum | 0.5 |
| Cetearyl alcohol (and) Ceteareth 20 | 1 |
| Glyceryl stearate (and) PEG 100 stearate | 4 |
| Preservatives | 9.5 |
| Licorice ext. | 0.05 |
| Galacturonic acid | 8 |
| Lactic acid | 5 |
| Sodium hydroxide q.s. to pH | 4 |
| Hydrogenated polyisobutene | 4 |
| Kojic acid | 1 |
| Ascorbyl palmitate | 0.5 |
| Tocopheryl linoleate | 0.5 |
| Purified water add to | 100 |

The composition of the above examples were tested and found to whiten skin. They also inhibit formation of dark skin spots.

Amongst representative acid derivatives there may be mentioned:

Sodium glycolate
Ammonium lactate
Pyruvic acid ethyl ester
Glucono-delta lactone
Acetyltriethyl citrate Of course various other functional derivatives of the kind defined herein can be used, and such derivatives were found to give an equivalent effect.

I claim:

1. A skin whitening cosmetic composition which also prevents formation of dark skin spots, which composition comprises in combination an oil soluble extract selected from the group consisting of an oil soluble extract of *Glycyrrhiza glabra* and an oil soluble extract of a plant species related thereto, together with a compound selected from the group consisting of alpha-hydroxy acids, beta-hydroxy acids, keto-acids amides thereof, ammonium salts thereof, inorganic salts thereof and esters thereof, wherein said composition is effective for whitening skin and for preventing formation of dark spots on skin when applied to the skin.

2. A composition according to claim 1, where the oil soluble plant extract is extracted from roots of *Glycyrrhiza glabra*.

3. A cosmetic composition according to claim 1, where the acid is selected from the group consisting of glycolic acid, lactic acid, malic acid, citric acid, Pyruvic acid, Tartaric acid, Salicylic acid, glucoronic acid, 2-hydroxy isobutyric acid, ethyl and methyl pyruvate.

4. A cosmetic composition according to claim 1, where the content of acid is between about 0.1% wt. and about 8% wt.

5. A cosmetic composition according to claim 1, which contains from about 0.05% wt to about 5 wt. % of concentrated plant extract.

6. A cosmetic composition according to claim 5, which contains from 0.05 wt. % to 0.2 wt. % concentrated plant extract.

7. A composition according to claim 1, further comprising at least one member selected from the group consisting of UVA filters, UVB filters, Vitamin E, Vitamin E derivatives, Vitamin C and Vitamin C derivatives.

8. A composition according to claim 1, wherein the *Glycyrrhiza glabra* extract contains about 10% glabridin, and the composition contains about 0.05% to about 3% of the extract.

9. A method for whitening human skin and for preventing formation of dark skin spots which comprises (1) applying to the skin an effective quantity for whitening human skin and for preventing formation of dark skin spots of a cosmetic composition comprising in combination an oil soluble plant extract of *Glycyrrhiza glabra* or related plant species, together with a member selected from the group consisting of alphahydroxy acids, beta-hydroxy acids, karo-acids, amides thereof, ammonium salts thereof, inorganic salts thereof and esters thereof, and (2) repeating step (1) as required for effectiveness.

10. A method according to claim 8, where the composition contains from about 0.05 wt. % to about 5 wt. % of the plant extract.

* * * * *